(12) United States Patent
Hoshino et al.

(10) Patent No.: US 6,410,251 B2
(45) Date of Patent: Jun. 25, 2002

(54) METHOD FOR DETECTING OR ASSAYING TARGET SUBSTANCE BY UTILIZING OXYGEN ELECTRODE

(75) Inventors: Fumihiko Hoshino; Osamu Asami; Hideo Nakane; Yukio Yamada, all of Aichi (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 0 days.

(21) Appl. No.: 09/440,585

(22) Filed: Nov. 15, 1999

(30) Foreign Application Priority Data

Nov. 18, 1998 (JP) ............................................. 10-328403

(51) Int. Cl.$^7$ ............................................. G01N 33/543
(52) U.S. Cl. ...................... 435/7.92; 435/7.9; 435/7.91; 435/772.2; 435/240; 435/972; 435/975; 436/514; 436/515; 436/518; 436/548; 436/819; 436/806; 204/400; 204/403; 422/82.01; 422/82.02
(58) Field of Search ................................ 435/7.9, 7.91, 435/7.92, 240, 172.2, 972, 975; 436/518, 548, 819, 514, 515, 806; 204/400, 403; 422/82.01, 82.02

(56) References Cited

U.S. PATENT DOCUMENTS

| | | | |
|---|---|---|---|
| 4,446,231 A | * 5/1984 | Self | ............................. 435/7 |
| 4,446,232 A | 5/1984 | Liotta | |
| 4,595,655 A | * 6/1986 | Self | ............................. 435/7 |
| 4,598,042 A | * 7/1986 | Self | ............................. 435/7 |
| 4,713,165 A | * 12/1987 | Conover et al. | |
| 4,855,240 A | 8/1989 | Rosenstein et al. | |
| 4,861,711 A | 8/1989 | Friesen et al. | |
| 4,956,275 A | * 9/1990 | Zuk et al. | ....................... 435/7 |
| 5,281,539 A | * 1/1994 | Schramm | |
| 5,573,920 A | * 11/1996 | Randle | |
| 5,580,794 A | * 12/1996 | Allen | ......................... 436/169 |
| 5,602,040 A | 2/1997 | May et al. | |
| 5,622,871 A | 4/1997 | May et al. | |
| 5,656,503 A | 8/1997 | May et al. | |
| 5,695,947 A | * 12/1997 | Guo et al. | ..................... 435/11 |
| 5,756,362 A | * 5/1998 | Durst et al. | ................. 436/518 |
| 5,789,154 A | * 8/1998 | Durst et al. | .................... 435/6 |
| 5,958,791 A | * 9/1999 | Roberts et al. | ............. 436/514 |
| 5,972,199 A | * 10/1999 | Heller et al. | ............. 205/777.5 |

OTHER PUBLICATIONS

Durst et al. (1992). Development of liposome–enhanced immuno–biosensing devices for field measurements of toxic substances. 2nd Bioelectroanalytical Symposium, Akademiai Kiaido, Budapest, pp. 15–32.*

(List continued on next page.)

*Primary Examiner*—Christopher L. Chin
(74) *Attorney, Agent, or Firm*—Oblon, Spivak, McClelland, Maier & Neustadt, P.C.

(57) ABSTRACT

A method for detecting or assaying one constituting member in a specific binding pair, for example, the antigen in an antigen/antibody pair, by utilizing specific binding such as binding between an antigen and an antibody, together with redox reaction for detecting a label, wherein an oxygen micro-electrode with a sensing surface area of 1 mm$^2$ or less is used; and an apparatus to which the method is applicable. According to the method and by using the apparatus, redox reaction for assaying the label can be completed in such a short time as several minutes. Therefore, an inexpensive disposable apparatus for household use can be realized.

25 Claims, 5 Drawing Sheets

OTHER PUBLICATIONS

Maggio (1987). Enzymes as immunochemical labels. In Enzyme–Immunoassay (ed. Maggio). CRC Press, Boca Raton, FL. pp. 53–70.*

Usmani (1995). Medical diagnostic reagents. In Encyclopedia of Chemical Technology, 4th Ed., vol. 16, Wiley & Sons, New York. pp. 88–107.*

Cobbold (1974). Transducers for Biomedical Measurements. Wiley & Sons, New York. p. 382.*

Aizawa et al. (1980). An enzyme Immunosensor for the electrochemical determination of the tunor antigen a–fetoprotein. Analytica Chimica Acta. 115:61–67.*

Kemeny (1997). Enzyme–linked immonoassay. In Immunochemistry 1, a Practical Approach (Eds. Johnstone et al.) Oxford University Press, New York.*

Boitieux et al. (1979). An "antibody electrode," preliminary report on a new approach in enzyme immunoassay. Clin. Chem. 25(2):318–321.*

Boitieux et al. (1981). Use of solid phase biochemistry for potentiometric exzyme immonoassay of oestradiol–17b–preliminary report. Clinica Chimica Acta. 113:175–182.*

* cited by examiner

METHOD FOR DETECTING OR ASSAYING TARGET SUBSTANCE BY UTILIZING OXYGEN ELECTRODE

BACKGROUND OF THE INVENTION

1. Field of the Invention

The present invention relates to a method for detecting or assaying a target substance by utilizing an oxygen electrode; more specifically, the invention relates to a method for detecting or assaying a target substance by utilizing specific binding, for example, between an antigen and an antibody or between a receptor and a ligand, the method comprising measuring the activity of a redox catalyst with which one of the antigen and the antibody or one of the receptor and the ligand has been labeled, by means of an oxygen electrode.

2. Description of the Related Art

Various methods for assaying each member in a pair of members specifically binding together (hereinafter referred to as a specific binding pair) have been known, wherein each member includes, for example, an antigen and an antibody in an antigen/antibody pair, and a receptor and a ligand for the receptor in a receptor/ligand pair. It is common to these methods in which one member of such specific binding pair is assayed as target substance A, that the presence or absence of the target substance A or the amount thereof can be determined by allowing the presence or absence of the target substance A or the amount thereof to be reflected as the binding amount of a labeled substance subjected to the specific binding and by detecting or assaying the presence or absence of the labeled substance bound or not bound or the amount thereof.

Various labels including enzyme labels, chemiluminescent labels, fluorescent labels, and radioactive labels, are used as the label. A method has been known for detecting or assaying redox reaction with a redox enzyme, for example, glucose oxidase as such enzyme label on the basis of chromogenic reaction or by means of an oxygen electrode. JP-A-5-72173 discloses a process of detecting an antigen or antibody in an antigen/antibody reaction solution under agitation while putting the antigen/antibody reaction solution into contact with an electrode. The process is disadvantageous, however, in that an enormous volume of such reaction solution is needed and should be agitated for detecting an antigen or antibody, which enforces laborious works and takes a long time, and additionally in that the process cannot be carried out readily at low cost in a simple manner by using a domestic disposable apparatus.

SUMMARY OF THE INVENTION

It is an object of the invention to provide a method for detecting or assaying a substance in body fluids, for example, urine and saliva, readily at low cost in a simple manner at home, wherein the substance can function as an indicator of various diseases; and an apparatus to which the method is applicable, for example, a domestic disposable apparatus.

In accordance with the invention, a method for detecting or assaying target substance A capable of specifically binding to specific substance B, by utilizing specific binding between the target substance A and the specific substance B and the reaction of a labeling catalyst is provided, the method comprising allowing a substrate of a redox catalyst to react with the redox catalyst of the target substance A, the specific substance B, third substance B' capable of specifically binding to the target substance A, or third substance A' capable of specifically binding to the specific substance B, in a porous support in contact with the sensing surface of an oxygen electrode, said substances B, B' and A' reflecting the amount of the target substance A, and said substances A, B, B' and A' having been directly labeled with the redox catalyst or bound to a substance labeled with the redox catalyst.

In accordance with the invention, the target substance A, the specific substance B, the third substance B' or the third substance A' is detected or assayed by using an oxygen electrode in contact with a porous support, where a redox catalyst with which the target substance A, the specific substance B, the third substance B' or the third substance A' is labeled, reacts with a substrate of the redox catalyst. Thus, the area of the sensing surface of the oxygen electrode or the depth of the reaction solution in the porous support can be made extremely small; and additionally, an open system can be used because the target substance A can be assayed in such a speedy manner. Therefore, a simple and inexpensive apparatus of small type can be constructed, including for example a domestic disposable apparatus.

The above and other objects, features and advantages of the present invention will become more apparent from the following description.

DETAILED DESCRIPTION OF THE INVENTION AND DESCRIPTION OF PREFERRED EMBODIMENTS

Figure 1:
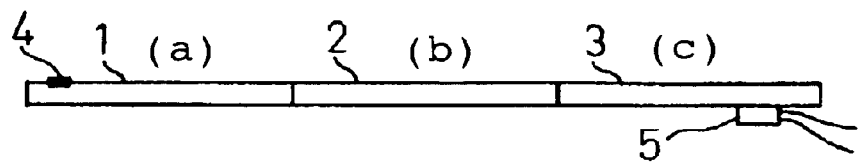
FIG. 1 is a schematic view of the apparatus of a first embodiment of the invention.

The invention will now be described in detail in the following specific embodiments.

In one preferred embodiment of the invention, one member composing a part of the porous support contains a substrate of the redox catalyst for redox reaction; the area of the sensing surface of an oxygen electrode in contact with the member is 1 $mm^2$ or less; and the thickness of the member on the oxygen electrode is 0.1 to 5 mm.

In accordance with the invention, the term target substance A means an antigen, an antibody, a ligand or a receptor or the like to be detected or assayed; the term specific substance B means a substance capable of specifically binding to the target substance A and includes, for example, antibodies against antigens, antigens against antibodies, ligands for receptors and receptors against ligands and the like. Furthermore, the term third substance A' means a substance capable of specifically binding to the specific substance B and includes the target substance A. The term third substance B' means a substance capable of specifically binding to the target substance A and includes the specific substance B.

In accordance with the invention, any antigen or any antibody against an antigen may be assayed. Antigens or antibodies contained in urine, saliva, blood and blood components such as serum and plasma, are particularly interesting assay subjects, indicating the presence of certain diseases; for example, urine albumin useful as a marker of diabetic nephropathy at an early stage can be assayed by the inventive method.

The invention relates to a method, in a general sense, for assaying a target substance A on the basis of specific binding reaction and redox reaction, comprising allowing the target substance A or a substance capable of specifically binding to a specific substance B, labeled with a redox catalyst, to react with a substrate of the redox catalyst in a member in contact with the sensing surface of an oxygen electrode, wherein preferably the area of the sensing surface of the oxygen electrode in contact with the member is 1 mm$^2$ or less and the thickness of the member on the oxygen electrode is 0.1 to 5 mm, more preferably 0.1 to 1 mm; and additionally, the invention also relates to an apparatus for practicing the method.

JP-A-5-72173 describes an immunoassay process of assaying an antigen by utilizing an oxygen electrode. According to the above method, the reaction solution is first placed in a container and is then put in contact with the surface of the oxygen electrode while the reaction solution is agitated. The process requires a costly apparatus of complex structure; the analytical procedures are not simple ones enough to domestically measure in a simple and easy manner. In accordance with the invention, assay can be completed in a very speedy manner because labeled molecules can be dispersed spontaneously (thermodynamically) without need of mechanical agitation, by using a very small oxygen electrode with a sensing surface of 1 mm$^2$ or less. Furthermore, the area of the sensing surface of the oxygen electrode is required to be 1 mm$^2$ or less, preferably 0.5 mm or less, most preferably 0.2 mm$^2$ or less, for example, 0.2 mm$^2$.

Putting a solution containing a reaction component labeled with a redox catalyst (but not containing any substrate of the redox catalyst) in contact with the sensing surface of an oxygen electrode, the oxygen electrode outputs a constant baseline electric current due to the presence of oxygen in the solution, which is kept in equilibrium with atmospheric oxygen; once a substrate of the redox catalyst is added to the solution, oxidation occurs to consume the oxygen in the solution and decrease the oxygen concentration in the solution. Consequently, the increase of the electric current output is measured with the oxygen electrode. In this case, the concentration of a redox catalyst label can be determined by measuring the initial velocity of the change of electric current or the value of electric current after a given time passes since the initiation of the reaction with the substrate added. The initial velocity of the change of electric current can satisfactorily be determined by measuring the change of electric current for 0.5 to 2 minutes, for example over about one minute. The value of electric current after a given time passes can satisfactorily be determined by measuring electric current for 3 to 5 minutes after the initiation of the reaction.

Because of such a very short time required for assaying under almost no influence of atmospheric air influx during the course of assaying, even an open system can be used for assaying. More specifically, oxygen consumption in a reaction solution due to substrate oxidation generally induces the dissolution of atmospheric oxygen into the solution, and this fact consequently compensates the decrease of the oxygen concentration following the progress of the oxidation reaction. For long-term assaying, the reaction should be carried out in a closed system so as to avoid such oxygen influx. For short-term assaying in accordance with the invention, the dissolution rate of atmospheric oxygen is much lower than the oxygen consumption rate due to the reaction in the solution. Thus, even an open system can satisfactorily function for the redox reaction.

In other words, the reaction between the redox catalyst and the substrate thereof can be progressed in a reaction solution in a porous support in contact with the sensing surface of the oxygen electrode. Accordingly, it is not required to seal a container charged with the reaction solution. The porous support includes filters for routine use in immunoassay, for example, cellulose filter, cellulose derivative filter, glass fiber filter, polyamide filter, polysulfone filter, polypropylene filter, polyvinyl chloride filter, porous ceramic, carbon fiber, and metal wool.

When the depth of the reaction solution (i.e. the thickness of a member necessary for the reaction in the porous support) in contact with the oxygen electrode is too small, atmospheric oxygen influx may influence the assay results. Thus, the depth of the reaction solution is 0.1 mm or more, but no specific advantage is brought about even when the depth thereof is very large. Accordingly, the depth of the reaction solution is preferably 0.1 mm to 5 mm; for practical convenience, the depth is 0.1 to 1 mm. Thus, a filter 0.1 to 1 mm thick is particularly preferable as the porous support.

Examples of the redox catalyst include redox enzymes and metal catalysts; preference is given to redox enzymes. Such redox enzymes and substrates (shown in parentheses) are, for example, as follows; glucose oxidase (glucose), xanthine oxidase (xanthine), amino acid oxidase (amino acid), ascorbic acid oxidase (ascorbic acid), acyl-CoA oxidase (acyl-CoA), cholesterol oxidase (cholesterol), galactose oxidase (galactose), oxalic acid oxidase (oxalic acid), and sarcosine oxidase (sarcosine).

The metal catalysts include, for example, platinum, gold and titanium oxide. Irradiation with light on for example titanium oxide ($TiO_2$) can trigger oxidation in the presence of organic substrates such as aldehyde.

The invention is applicable to various assay systems in which specific binding pairs such as an antigen/antibody pair participate.

In one embodiment, the method comprises steps of:
(1) putting a sample solution expected to contain target substance A in contact. with specific substance B labeled with a redox catalyst in a solution, thereby allowing the target substance A and the specific substance B to specifically bind together;
(2) putting the solution resulting from the step (1) into contact with a member to which a substance capable of specifically binding to the specific substance B is immobilized to immobilize and remove an unreacted specific substance B in (1);

(3) putting the reaction solution containing the target substance A specifically bound to the labeled specific substance B in contact with the sensing surface of an oxygen electrode.

The method is carried out with an apparatus shown, for example, in FIG. 1. The apparatus comprises: element (a) composed of member 1 containing specific substance B labeled with a redox catalyst therein and having a sample addition port 4 at a part of the element (a); element (b) composed of member 2 to which third substance A' capable of specifically binding to the labeled specific substance B is immobilized; and element (c) composed of member 3 containing a substrate for the redox catalyst therein and being in contact with an oxygen electrode 5 having a sensing surface area of 1 mm$^2$ or less, wherein the sample addition port 4 of the element (a) is in fluid communication via capillarity through the element (b) with the element (c) in contact with the oxygen electrode.

In the method and the apparatus described above, the third substance A' most simply means the same substance as the target substance A. However, when the target substance A is, for example, a glycoprotein present in body fluids, the third substance A' may include non-glycosylated proteins prepared by genetic engineering, fragments of the above proteins, and proteins with a modification of the amino acid sequence thereof. However, the third substance A' is required to be capable of binding to an antibody against the target antigen substance A.

With reference to the schematic view of the apparatus in FIG. 1, the method is now described, by using an antigen as the target substance A, an antibody against the target antigen substance A as specific substance B, a substance capable of specifically binding to the labeled specific substance B as an antigen, and glucose oxidase as the redox catalyst.

In FIG. 1, 1 represents a member of the element (a) of the above apparatus, and a sample addition port 4 is arranged on the member 1. The member 1 contains a glucose oxidase-labeled antibody as the specific substance B. 2 represents a member of the element (b) of the above apparatus, to which the third substance A' capable of specifically binding to the antibody is immobilized. An antigen, for example, is immobilized as the third substance A'. 3 represents a member of the element (c) of the above apparatus, containing glucose as a catalyst for glucose oxidase and being put into contact with oxygen electrode 5 having a sensing surface area of 1 mm$^2$ or less.

Once a sample solution containing the target antigen substance is added into the sample addition port 4, the sample solution is dispersed via capillarity into the member 1 of the element (a), to come into contact with a glucose oxidase-labeled antibody placed in the member 1 to induce binding between the antigen and the antibody, to generate an antigen/antibody complex. Because the glucose oxidase-labeled antibody is contained at an excess amount in the member 1 of the element (a), the target antigen substance quantitatively binds to the glucose oxidase-labeled antibody, so that the glucose oxidase-labeled antibody partially remains unreactive and is kept therein.

After the reaction in the member 1 of the element (a), the reaction solution is then transferred via capillarity to the member 2 of the element (b). When the volume of the sample solution is too small to be distributed in the whole apparatus, an appropriate aqueous medium, for example a buffer, is additionally poured from the sample addition port 4 after the sample solution is added, to help the transfer of the reactive substances. The unreactive glucose oxidase-labeled antibody in the member 1 of the element (a) binds to and is captured by the antigen immobilized to the member 2 of the element (b) Then, only the complex of the target antigen substance and the glucose oxidase-labeled antibody can transfer to the member 3 of the element(c).

Subsequently, the glucose oxidase in the complex oxidizes glucose placed in the member 3 of the element (c), so that the oxygen concentration in the solution decreases in the member 3 of the element (c); and then, the change of the oxygen concentration is detected and measured with the oxygen electrode 5.

According to another embodiment of the invention, a method is provided which comprises steps of:
(1) putting target substance A into contact with specific substance B labeled with a redox catalyst in a solution, thereby allowing the target substance A and the specific substance B to bind together;
(2) feeding the resulting solution from the step (1) to a member to which third substance B' capable of specifically binding to the target substance A is immobilized and which is in contact with the sensing surface of an oxygen electrode, whereby the labeled specific substance B binding to the target substance A as recovered from the step (1) can be immobilized through the third substance B' on the member;
(3) removing the labeled specific substance B not binding to the target substance A in the step (1) from the member in contact with the sensing surface of the oxygen electrode described in the step (2); and
(4) putting a substrate of the redox catalyst into contact with the labeled specific substance B immobilized in the step (2) to the member in contact with the sensing surface of the oxygen electrode.

The method can be conducted with, for example, an apparatus comprising:
element (a) containing specific substance B labeled with a redox catalyst therein and having a sample addition port at a part of the element (a);
element (b) to which third substance B' is immobilized and which is in contact with an oxygen electrode with a sensing surface having an area of 1 mm$^2$ or less; and
liquid-absorbing element (c), wherein the sample addition port of the element(a) is in fluid communication via capillarity through the element(b) with the element(c).

In the above method and the apparatus, any third substance B' capable of specifically binding to the target substance A is satisfactory, with no limitation; when the target substance A is an antigen, the third substance B' may be a second antibody against the target antigen substance A, which is different from the labeled antibody B. For example, one antibody may be monoclonal, while the other antibody may be polyclonal; otherwise, these antibodies may be two types of monoclonal antibodies with different epitopes.

Figure 2:
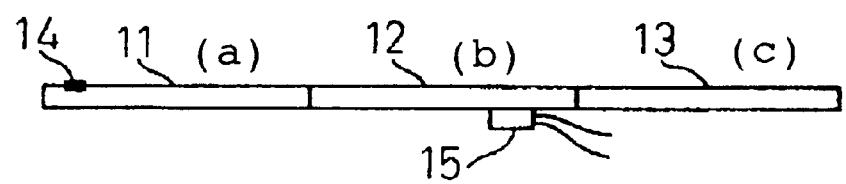
FIG. 2 is a schematic view of the apparatus of a second embodiment of the invention.

With reference to the schematic view of the apparatus in FIG. 2, the embodiment is now described, by using an antigen as the target substance A, an antibody against the target antigen substance A as the specific substance B, glucose oxidase as the redox catalyst and glucose as a substrate of the redox catalyst.

In FIG. 2, 11 represents a member of the element (a) comprising sample addition port 14, wherein the member 11 contains a glucose oxidase-labeled antibody against the target substance A; 12 represents a member of the element (b) of the apparatus, to which a second antibody as third substance B' capable of specifically binding to the target substance A, is immobilized and which is in contact with an oxygen electrode having a sensing surface area of 1 mm$^2$ or less; 13 represents a member of the element (c) and absorbs liquid.

Once a sample solution containing the target antigen substance is added through the sample addition port 14 of the member 11 of the element (a), the sample solution is dispersed via capillarity into the member 11 of the element (a). Because a glucose oxidase-labeled antibody (a first antibody) against the target antigen substance is placed in the member 11 of the element (a), the target antigen substance immunologically binds to the labeled antibody, to form an antigen/antibody complex. Because the labeled antibody is present in an excess amount, the target antigen substance quantitatively binds to the labeled antibody, while a part of the labeled antibody remains unreactive.

Then, the antigen/antibody complex formed in the member 11 of the element (a) and the resulting unreactive labeled antibody are transferred through the transfer of the sample solution via capillarity to the member 12 of the element (b) When the volume of the sample solution is not enough to transfer the reaction product, a buffer and the like are additionally added through the sample addition port 14 to help the transfer.

Because a second antibody is immobilized to the member 12 of the element (b), the target antigen substance in the antigen/antibody complex transferred from the member 11 of the element (a) binds to the immobilized second antibody, so that the labeled antibody (first antibody) is immobilized, through the target antigen substance and the preliminarily immobilized second antibody, to the member 12 of the element (b). By subsequently adding glucose as a substrate of the labeling glucose oxidase to the element (b), glucose oxidase initiates to oxidize glucose and thereby decrease the oxygen concentration in the solution; and then, the change of the oxygen concentration is detected with the oxygen electrode 15.

In this embodiment, the target antigen substance can be assayed at high sensitivity because the target substance is accumulated in the member 12 of the element (b) in contact with the oxygen electrode 15.

In a third embodiment of the invention, a method is provided which comprises steps of:
(1) mixing target substance A with third substance A', being capable of specifically binding to specific substance B and labeled with a redox catalyst;
(2) feeding the resulting mixture from the step (1) to a member to which specific substance B is immobilized thereto and which is in contact with the sensing surface of an oxygen electrode, whereby the target substance A and the third substance A' bind competitively to the specific substance B immobilized to the member in contact with the sensing surface of the oxygen electrode;
(3) removing the target substance A and the third substance A', both not binding at the step (2) to the specific substance B immobilized; and
(4) putting a substrate of the redox catalyst into contact with the member in contact with the sensing surface of the oxygen electrode.

Figure 3:
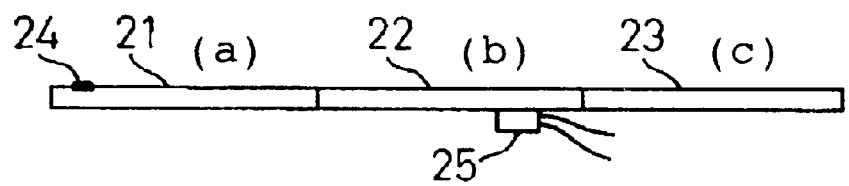
FIG. 3 is a schematic view of the apparatus of a third embodiment of the invention.

The method can be practiced with the apparatus shown in FIG. 3, for example, comprising:
element (a) containing the third substance A' labeled with a redox catalyst therein and sample addition port at a part thereof;
element (b) immobilizing the specific substance B and being in contact with an oxygen electrode having a sensing surface area of 1 $mm^2$ or less; and
liquid-absorbing element (c), wherein the sample addition port of the element (a) is in fluid communication via capillarity through the element (b) with the element (c).

In the method and the apparatus described above, the term third substance A' most straightforwardly means the same substance as the target substance A. When the target substance is a glycoprotein present in body fluids, however, the third substance A' satisfactorily includes non-glycosylated proteins prepared by genetic engineering, fragments of the above proteins, and proteins with a modification of the amino acid sequence thereof. However, the third substance A' is required to be able to bind to an antibody against an antigen as the target substance A.

With reference to the schematic view of the apparatus in FIG. 3, 21 represents a member of the element (a) of the apparatus and contains a substance capable of specifically binding to an antibody against the target antigen substance, for example the same substance as the target antigen substance or a modification thereof, which is further labeled with glucose oxidase and the like; sample addition port 24 is arranged on the member 21. 22 represents a member of the element (b) of the apparatus, to which an antibody against the target antigen substance is immobilized and which is in contact with the sensing surface of oxygen electrode 25. 23 represents liquid-absorbing element (c).

For assaying, a sample solution containing an antigen as the target substance is added through the sample addition port 24 of the member 21 of the element (a) The sample solution added is dispersed via capillarity into the member 21 of the element (a), to be mixed with a specifically binding substance contained therein, for example labeled antigen. Following the transfer of the sample solution, the mixture is transferred via capillarity to the member 22 of the element (b). When the volume of the sample solution is not enough to transfer the reactive substance, a transfer medium such as buffer can be added through the sample addition port 24.

Then, an unknown amount (concentration) of the target antigen substance transferred to the member 22 of the element (b) and a known amount (concentration) of the labeled antigen competitively bind to the antibody immobilized to the member 22 of the element (b), so that the labeled antigen at an amount (at a concentration) in reverse proportion to the amount (the concentration) of the target substance derived from the sample binds to and is captured by the immobilized antibody. The target antigen substance and the labeled antigen in free state are transferred via capillarity to liquid-absorbing element (c). When glucose is added to the member 22 of the element (b), glucose oxidase immobilized to the member 22 of the element (b) oxidizes glucose, which causes the decrease in the oxygen concentration. The decrease is detected with oxygen electrode 25 in contact with the member 22 of the element(b).

A modification of the embodiment comprises mixing a sample solution containing a target antigen substance with a labeled antigen in a test tube and subsequently adding the resulting mixture directly to the member 22 of the element (b) in FIG. 3, without using the member 21 of the element (a) in FIG. 3.

In a fourth embodiment of the invention, a method is provided which comprises steps of:
(1) permitting third substance A' identical to the target substance A or a substance capable of specifically binding to specific substance B after the third substance A' is labeled with a redox catalyst, to bind to specific substance B immobilized to a member;
(2) adding a sample containing the target substance A to the member, to allow the target substance A and the labeled third substance A', to compete for the specific substance B immobilized to the member, to partially free the labeled third substance A' in an amount depending on the amount of the target substance A;

(3) separating the labeled third substance A' in free state from the labeled third substance A' in binding state; and (4) allowing the labeled third substance A' in free state or in binding state to react with a substrate of the labeling redox catalyst in a member in contact with the sensing surface of an oxygen electrode.

Figure 4:
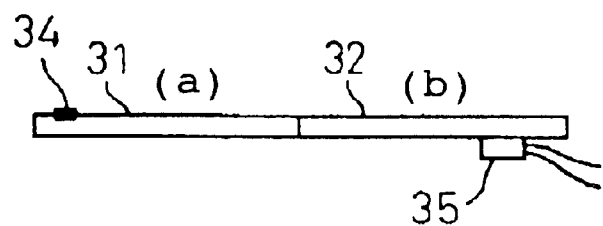
FIG. 4 is a schematic view of the apparatus of one example of a fourth embodiment of the invention.

For assaying the labeled third substance A' in free state at the step (4) of the method, for example, the apparatus shown in FIG. 4 is used, comprising:

element (a) composed of a member to which the specific substance B is immobilized, where third substance A' which is identical to the target substance A or a substance capable of specifically binding to the specific substance B and which is labeled with a redox catalyst, binds to the immobilized specific substance B, wherein a part of the member composes a sample addition port; and element (b) containing therein a substrate for the redox catalyst and being in contact with the oxygen electrode with a sensing surface having an area of 1 $mm^2$ or less, wherein the sample addition port of the element (a) is in fluid communication via capillarity with the element (b) in contact with the oxygen electrode.

In the method and the apparatus, the term third substance A' most straightforwardly means the same substance as the target substance. When the target substance is a glycoprotein present in body fluids, however, the third substance A' satisfactorily includes non-glycosylated proteins prepared by genetic engineering, fragments of the above proteins, and proteins with a modification of the amino acid sequence thereof. However, the third substance A' is required to be able to bind to an antibody against the antigen as the target substance.

With reference to the schematic view of the apparatus in FIG. 4, 31 represents a member of the element (a), to which the specific substance B is immobilized; the third substance A' identical to the target substance A or a substance capable of specifically binding to the specific substance B, which is labeled with a redox catalyst, is bound to the specific substance B immobilized to the member of the element (a). A part of the member 31 of the element (a) constitutes the sample addition port 34. 32 represents a member of element (b) which is in contact with the sensing surface of the oxygen electrode having an area of the sensing surface of 1 $mm^2$ or less.

For assaying, a sample solution containing a target substance (for example, an antigen) is added to the sample addition port 34 of the member 31 of the element (a), whereby the target substance A in the sample solution and the labeled third substance A' (typically the same substance as the target substance A, for example, an antigen labeled with a redox catalyst) bound to specific substance B, an antibody, immobilized to the member 31 of the element (a) compete against the immobilized antibody and a part of the labeled third substance A' bound to the immobilized antibody is released, depending on the amount of the target antigen substance.

The sample solution added through the sample addition port 34 is transferred via capillarity through the member 31 of the element (a) to member 32 of the element (b), so that the labeled third substance A' (antigen) released is transferred to the member 32 of the element (b). When the sample solution is not enough to transfer the labeled third substance A' released to the member 32 of the element (b), a transfer medium such as buffer can be added through the sample addition port 34.

A substrate (for example, glucose) of the redox catalyst is contained in (is added to) the element (b), where the substrate reacts with the redox catalyst-labeled third substance A' transferred to the element (b) to decrease the oxygen concentration. The decrease is detected with oxygen electrode 35 in contact with the member 32 of the element (b).

Figure 5:
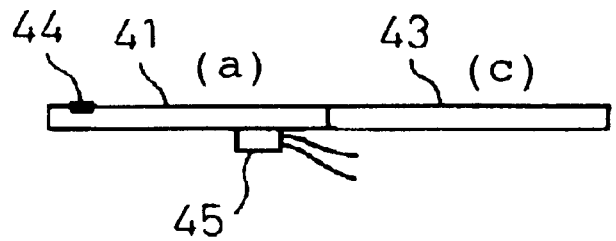
FIG. 5 is a schematic view of the apparatus of another example of a fourth embodiment of the invention.

For assaying the labeled third substance A' in binding state at the step (4) in the fourth embodiment, for example, an apparatus shown in FIG. 5 is used, comprising:

element (a) of a member to which the specific substance B is immobilized, where third substance A' identical to the target substance A or a substance capable of specifically binding to the specific substance B, which is labeled with a redox catalyst, binds to the immobilized specific substance B, wherein a part of the member composes a sample addition port and the member is in contact with an oxygen electrode having a sensing surface area of 1 $mm^2$ or less; and liquid-absorbing element (b), wherein the sample addition port of the element (a) is in fluid communication via capillarity with the element (b).

In the method and the apparatus described above, the term third substance A' most straightforwardly means the same substance as the target substance. When the target substance is a glycoprotein present in body fluids, however, the third substance A' satisfactorily includes non-glycosylated proteins prepared by genetic engineering, fragments of the above proteins, and proteins with a modification of the amino acid sequence thereof. However, the third substance A' is a required to be able to bind to an antibody against the antigen as the target substance.

With reference to the schematic view of the apparatus in FIG. 5, 41 represents a member of the element (a), to which the specific substance B is immobilized; and third substance A' identical to the target substance A or a substance capable of specifically binding to the specific substance B, which is labeled with a redox catalyst, binds to the specific substance B immobilized to the element (a). A part of the member 41 of the element (a) composes sample addition port 44. Oxygen electrode 45 is in contact with the member 41 of the element (a). 43 represents element (c) as liquid-absorbing element.

For assaying, a sample solution containing a target substance (for example, an antigen) is added via the sample addition port 44 of the member 41 of the element (a), whereby the target antigen substance A in the sample solution and the labeled third substance A' (typically including the same material as the target substance A, for example an antigen labeled with a redox catalyst) bound to specific substance B (for example, an antibody against the antigen) immobilized to the member material 41 of the element (a), competitively bind to the immobilized antibody, so that the labeled third substance A' (antigen) is partially released, depending on the amount of the target antigen substance.

The sample solution added through the sample addition port 44 is transferred via capillarity into member 43 of the liquid-absorbing element (c). Following the transfer, the labeled third substance A' released is transferred to member 43 of the liquid-absorbing element (c). When the volume of the sample solution is not enough to transfer the released third substance A' to the member 43 of the element (c), a transfer medium such as buffer can be added through the sample addition port 44.

Then, a substrate of the redox catalyst, for example, a glucose solution, is added to the member 41 of the element (a). In such a manner, the substrate (glucose) reacts with the redox catalyst (for example, glucose oxidase) bound to the substance A' as it is still bound to the antibody immobilized to the member 41 of the element (a), to decrease the oxygen concentration in the member 41 of the element (a), which decrease is detected with the oxygen electrode 45 in contact with the member 41 of the element (a).

The invention is described in the applicable four embodiments, but is not limited to them. The invention is applicable to various immunoassay modes.

In the apparatuses shown in FIGS. 1 to 5, for example, any material capable of liquid transfer via capillarity is applicable to the elements (a), (b) and (c); the elements (a), (b) and (c) may be prepared by using, for example, filters such as cellulose filter pieces.

Figure 6A:
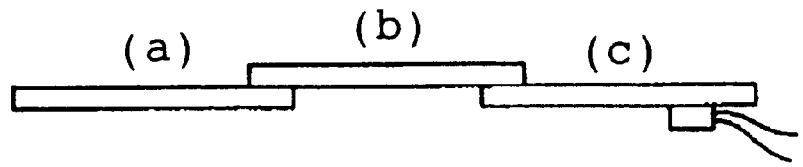
FIGS. 6A and 6B are schematic views of elements (a), (b) and (c) of the inventive apparatus, prepared separately and arranged superposedly.
Figure 6B:
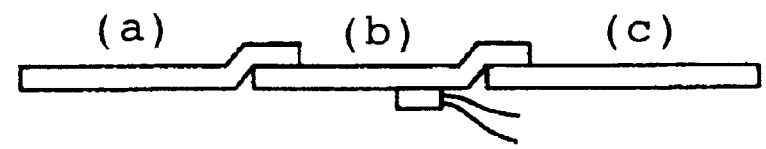

Alternatively, porous materials such as cellulose powder, cellulose derivatives, glass fiber, fluorine compound materials, polyamide, polystyrene, polypropylene, polyvinyl chloride, porous ceramic, carbon fiber and metallic wool may be molded or filled in a tube shape (column shape). Alternatively, the elements (a), (b) and (c) may be prepared independently from different materials as shown in FIGS. 6A and 6B, for example, filter pieces; by laminating the ends thereof together, fluid communication via capillarity can be accomplished.

Figure 7A:
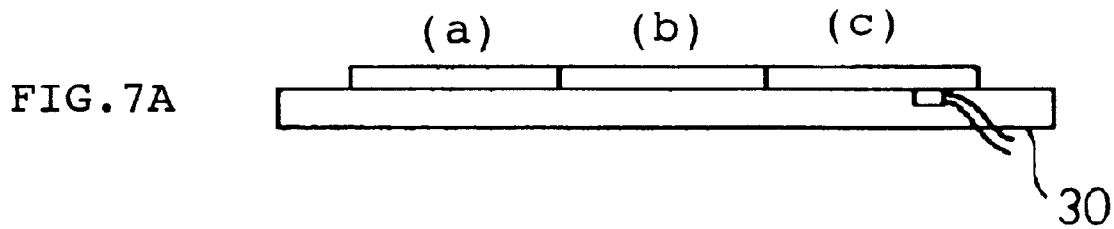
FIGS. 7A, 7B and 7C are schematic views of separate elements (a), (b) and (c) of the inventive apparatus, as arranged on support 30.
Figure 7B:
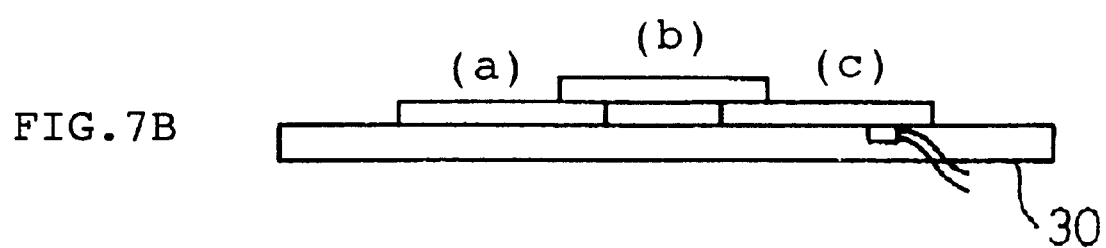
Figure 7C:
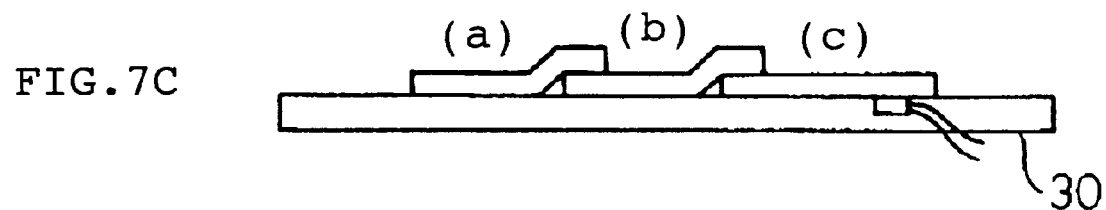

In accordance with the invention, the term fluid communication via capillarity means that a sample solution or another transfer medium (liquid) can be transferred via capillarity. Additionally, the elements (a), (b) and (c) may be prepared by using filter papers singly or in combination with a liquid-impermeable support 30, for example, synthetic resin plate to improve the strength; on the surface of the support 30, the elements are arranged as shown in FIGS. 7A, 7B, and 7C.

EXAMPLE

The invention is specifically described in detail in the following example.

Example 1

At a model experiment for the assay of urine albumin as a diabetic nephropathy indicator useful for early diagnosis of the disease, human urine and aqueous buffer solutions, at albumin concentrations of 0, 20, 50, 100 and 200 $\mu$g/ml, were prepared by adding albumin to human urine and a control buffer.

A BALB/c mouse was sensitized with human albumin; splenocytes from the spleen resected were fused with mouse shemoma cells to create hybridomas generating antialbumin antibodies. Among the hybridomas, a hybridoma generating an antibody with high affinity was screened and prepared as monoclonal. The hybridoma cell was injected into the mouse abdominal cavity; several weeks later, the ascites fluid was recovered; and then, the mouse anti-human albumin monoclonal antibody was recovered from the ascites fluid, which was purified on a Protein A-fixed column.

The anti-human albumin monoclonal antibody thus recovered was labeled with glucose oxidase as follows. 100 $\mu$l of 0.1 M $NaIO_3$ was added to a solution of 2 mg of glucose oxidase in 0.8 ml of water, for reaction at 25° C. for 30 minutes. 50 $\mu$l of ethylene glycol was added to the resulting reaction mixture, for incubation at 25° C. for 5 minutes, followed by desalting with 2 mM $CH_3COOH$, pH 4.4 and gel filtration, to recover formylated glucose oxidase. A solution of 10 mg of the monoclonal antibody in 2 ml PBS and 100 $\mu$l of 1M $NaCO_3$ (pH 9.5) was added to 2 mg of the formylated glucose oxidase, for reaction at 25° C. for 2 hours. Subsequently, 40 $\mu$l of 4 mg/ml $NaBH_4$ was added to the resulting reaction mixture, for reaction at 4° C. for 2 hours; the resulting reaction mixture was subjected to concentration and gel filtration, to recover a mouse anti-human albumin monoclonal antibody labeled with glucose oxidase.

The solutions of albumin with various concentrations (0 $\mu$g/ml to 200 $\mu$g/ml) in human urine and in the buffer as prepared above were independently reacted with the glucose oxidase-labeled antibody prepared in the aforementioned manner; the resulting reaction solutions were subsequently passed through a column immobilizing human albumin thereto, whereby unreactive glucose oxidase-labeled antibody was removed, to recover a solution containing the labeled antibody bound to albumin. On the other hand, an oxygen electrode with a sensing area of 0.04 $mm^2$ was placed on a water non-absorbable carrier; a glucose solution was absorbed into a filter paper, which was then dried; by using the resulting filter paper, the oxygen electrode was covered.

Figure 8:
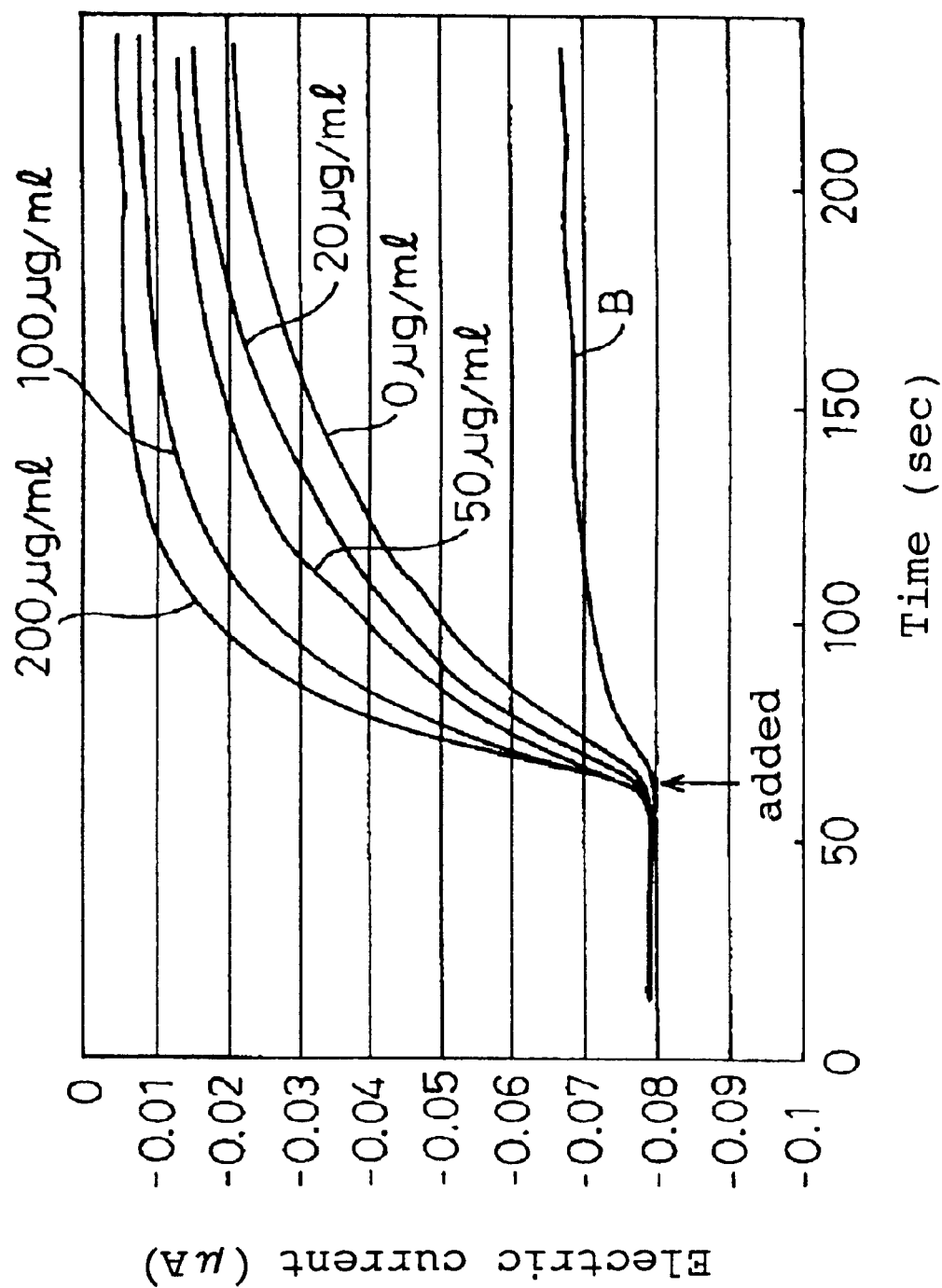
FIG. 8 shows graphs depicting the change with time of output electric current measured with an oxygen electrode when human albumin is assayed as a target antigen substance.

The solution containing the labeled antibody bound to albumin was dropwise added to the filter paper; prior to and after the dropwise addition, the output electric current was measured successively with the oxygen electrode, which was then recorded. Alternatively, a buffer was dropwise added to a filter paper not treated in the aforementioned manner; the resulting filter paper was used to define base line B. FIG. 8 shows the results of albumin assay in the buffer solutions. It was confirmed that the initial velocity of the change of electric current as well as the change of electric current after a given time passed was increased, depending on the albumin concentration.

Figure 9:
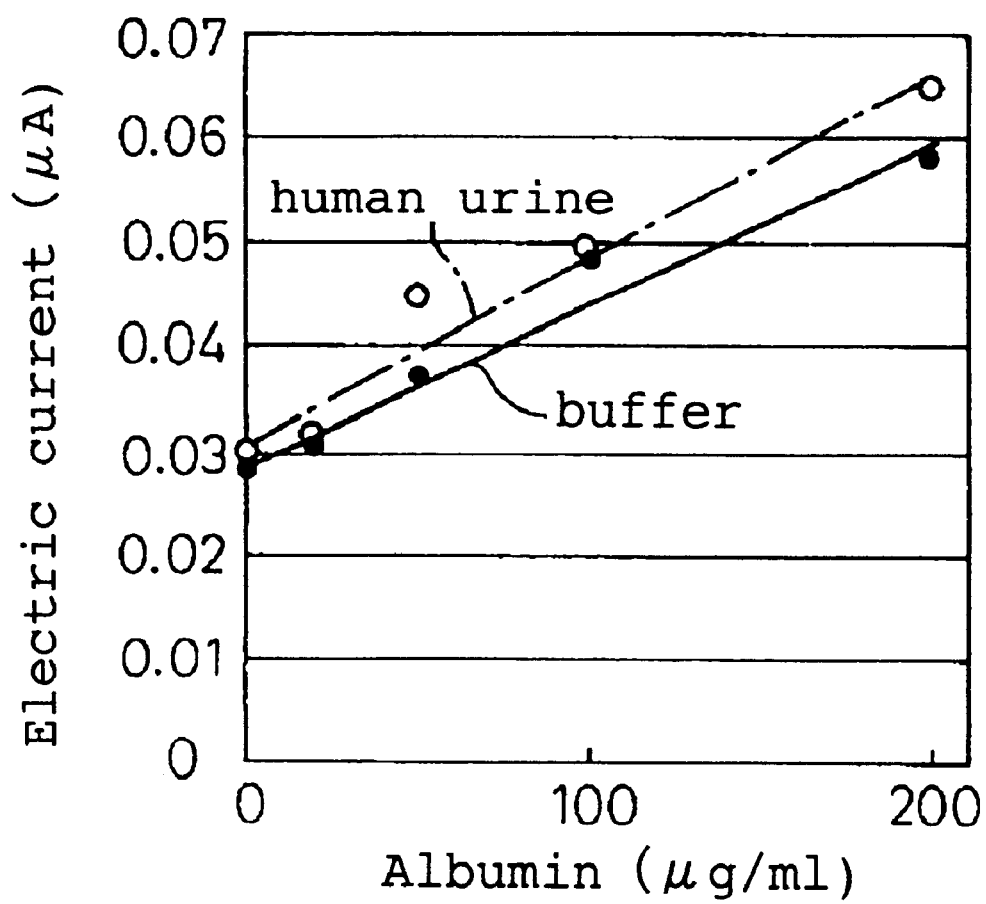
FIG. 9 shows graphs depicting the relation between the concentration of human albumin as a target antigen substance assayed by the inventive method and the change of the output electric current as measured with an oxygen electrode.

FIG. 9 shows graphically the relation between the change of electric current 100 seconds after the addition of the albumin solutions in human urine and in the buffer on the axis of ordinate and the albumin concentration on the axis of abscissa. The graphs show that the results obtained by using human urine are fairly identical to the results obtained by using the buffer. Thus, it was confirmed that the inventive assay method is not influenced with contaminants in human urine.

In FIG. 9, the difference between the results obtained by using human urine and the results obtained by using the buffer is possibly ascribed to the albumin originally contained in human urine.

While the preferred embodiments have been described, variations thereto will occur to those skilled in the art within the scope of the inventive concepts which are delineated by the following claims.

What is claimed is:

1. A method for detecting or assaying target substance A capable of specifically binding to specific substance B, comprising:
   (1) feeding a sample solution expected to contain a target substance A to a porous support to allow the target substance A to react with a specific substance B labeled with a redox catalyst;
   (2) allowing the sample solution from step (1) to migrate to a member composing a part of the porous support where a third substance A' capable of specifically binding to specific substance B is immobilized, thereby immobilizing the specific substance B in a free state;
   (3) allowing the sample solution from step (2) to migrate to a sensing surface of an oxygen electrode in contact with a part of the porous support to bring the solution and a substrate of the redox catalyst into contact with the sensing surface of the oxygen electrode, and detecting or measuring an activity of the redox catalyst contained in the solution as a change of an electric current of the oxygen electrode due to consumption of the oxygen in the solution, wherein the area of the sensing surface of the oxygen electrode is 1 mm$^2$ or less, and the thickness of the member on the oxygen electrode is 0.1 to 5 mm; and (4) detecting the presence or concentration of said target substance A based on the change of the electric current.

2. A method for detecting or assaying target substance A capable of specifically binding to a specific substance B, comprising:

(1) feeding a sample solution expected to contain a target substance A to a porous support to allow the target substance A to react with a specific substance B labeled with a redox catalyst;

(2) allowing the sample solution from step (1) to migrate to a member composing a part of the porous support where a third substance B' capable of specifically binding to specific substance A is immobilized, thereby immobilizing the specific substance B bound to the target substance A;

(3) bringing the part of the porous support to which the specific substance B is immobilized in step (2) and a substrate of the redox catalyst into contact with the sensing surface of the oxygen electrode, and detecting or measuring an activity of the redox catalyst as a change of an electric current of the oxygen electrode due to consumption of the oxygen in the solution, wherein the area of the sensing surface of the oxygen electrode is 1 mm$^2$ or less, and the thickness of the member on the oxygen electrode is 0.1 to 5 mm; and (4) detecting the presence or concentration of said target substance A based on the change of the electric current.

3. A method for detecting or assaying target substance A capable of specifically binding to specific substance B, comprising:

(1) adding a known amount of third substance A' to a sample solution expected to contain a target substance A, said third substance A' being capable of specifically binding to specific substance B and labeled with a redox catalyst;

(2) feeding the sample solution from step (1) to a member composing a part of a porous support where a specific substance B is immobilized, thereby allowing the target substance A and the third substance A' to competitively react with and immobilize to the specific substance B;

(3) bringing the part of the porous support to which the third substance A' is immobilized in step (2) and a substrate of the redox catalyst into contact with the sensing surface of the oxygen electrode, and detecting or measuring an activity of the redox catalyst as a change of an electric current of the oxygen electrode due to consumption of the oxygen in the solution, wherein the area of the sensing surface of the oxygen electrode is 1 mm$^2$ or less, and the thickness of the member on the oxygen electrode is 0.1 to 5 mm; and (4) detecting the presence or the concentration of the target substance A based on the change of the electric current.

4. A method for detecting or assaying target substance A capable of specifically binding to specific substance B, comprising:

(1) allowing a third substance A' capable of specifically binding to specific substance B and labeled with a redox catalyst to react with a specific substance B immobilized to a member composing a part of a porous support to immobilize a known amount of the third substance A';

(2) feeding a sample solution expected to contain a target substance A to said member composing a part of the porous support, and allowing the target substance A and the immobilized third substance A' to compete with each other and to partially free the third substance A' in an amount depending on the amount of the target substance A;

(3) bringing the part of the porous support containing the still immobilized third substance A' after step (2) and a substrate of the redox catalyst into contact with a sensing surface of an oxygen electrode, and detecting or measuring an activity of the redox catalyst as a change of an electric current of the oxygen electrode due to consumption of the oxygen in the solution, or (3') allowing the sample solution from step (2) containing the freed third substance A' to migrate to a sensing surface of an oxygen electrode in contact with a part of the porous support to bring the solution and a substrate of the redox catalyst into contact with the sensing surface of the oxygen electrode, and detecting or measuring an activity of the redox catalyst contained in the solution as a change of an electric current of the oxygen electrode due to consumption of the oxygen in the solution, wherein the area of the sensing surface of the oxygen electrode is 1 mm$^2$ or less, and the thickness of the member on the oxygen electrode is 0.1 to 5 mm; and (4) detecting the presence or the concentration of the target substance A based on the change of the electric current.

5. The method according to claim 2, wherein one of the target substance A and the specific substance B is an antigen and the other is an antibody.

6. The method according to claim 3, wherein one of the target substance A and the specific substance B is an antigen and the other is an antibody.

7. The method according to claim 4, wherein one of the target substance A and the specific substance B is an antigen and the other is an antibody.

8. The method according to claim 2, wherein one of the target substance A and the specific substance B is a receptor and the other is a ligand.

9. The method according to claim 3, wherein one of the target substance A and the specific substance B is a receptor and the other is a ligand.

10. The method according to claim 4, wherein one of the target substance A and the specific substance B is a receptor and the other is a ligand.

11. The method according to claim 2, wherein the redox catalyst is a redox enzyme or a metal catalyst.

12. The method according to claim 3, wherein the redox catalyst is a redox enzyme or a metal catalyst.

13. The method according to claim 4, wherein the redox catalyst is a redox enzyme or a metal catalyst.

14. The method according to claim 11, wherein the redox catalyst is glucose oxidase.

15. The method according to claim 12, wherein the redox catalyst is glucose oxidase.

16. The method according to claim 13, wherein the redox catalyst is glucose oxidase.

17. The method according to claim 1, wherein the redox catalyst is selected from the group consisting of xanthine oxidase, amino acid oxidase, ascorbic oxidase, acely-CoA oxidase, cholesterol oxidase, galactose oxidase, oxalic oxidase, and sarcosine oxidase.

18. The method according to claim 11, wherein the redox catalyst is selected from the group consisting of xanthine oxidase, amino acid oxidase, ascorbic oxidase, acely-CoA oxidase, cholesterol oxidase, galactose oxidase, oxalic oxidase, and sarcosine oxidase.

19. The method according to claim 12, wherein the redox catalyst is selected from the group consisting of xanthine oxidase, amino acid oxidase, ascorbic oxidase, acely-CoA oxidase, cholesterol oxidase, galactose oxidase, oxalic oxidase, and sarcosine oxidase.

20. The method according to claim 13, wherein the redox catalyst is selected from the group consisting of xanthine oxidase, amino acid oxidase, ascorbic oxidase, acely-CoA oxidase, cholesterol oxidase, galactose oxidase, oxalic oxidase, and sarcosine oxidase.

21. The method according to claim 1, wherein the area of the sensing surface of the oxygen electrode is 0.5 mm$^2$ or less and the thickness of the member on the oxygen electrode is 0.1 to 1 mm.

22. The method according to claim 1, wherein one of the target substance A and the specific substance B is an antigen and the other is an antibody.

23. The method according to claim 1, wherein one of target substance A and the specific substance B is a receptor and the other is a ligand.

24. The method according to claim 1, wherein the redox catalyst is a redox enzyme or a metal catalyst.

25. The method according to claim 24, wherein the redox enzyme is glucose oxidase.

* * * * *

UNITED STATES PATENT AND TRADEMARK OFFICE
CERTIFICATE OF CORRECTION

PATENT NO.    : 6,410,251 B2                                    Page 1 of 1
DATED         : June 25, 2002
INVENTOR(S)   : Hoshino et al.

It is certified that error appears in the above-identified patent and that said Letters Patent is hereby corrected as shown below:

<u>Title page,</u>
Item [45] and Notice information should read as follows:

-- [45]  **Date of Patent:  *Jun. 25, 2002**

[*] Notice:  This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Signed and Sealed this

Fifteenth Day of April, 2003

JAMES E. ROGAN
*Director of the United States Patent and Trademark Office*